(12) United States Patent
Shiber

(10) Patent No.: US 7,316,697 B2
(45) Date of Patent: Jan. 8, 2008

(54) VESSEL CLEANING SYSTEM WITH ASYMMETRICAL AUTO RETRACTING AGITATOR

(76) Inventor: Samuel Shiber, 365 Kearney Cir., Manchester, NH (US) 03104

( * ) Notice: Subject to any disclaimer, the term of this patent is extended or adjusted under 35 U.S.C. 154(b) by 614 days.

(21) Appl. No.: 10/423,677

(22) Filed: Apr. 25, 2003

(65) Prior Publication Data

US 2003/0187468 A1 Oct. 2, 2003

Related U.S. Application Data

(63) Continuation-in-part of application No. 10/252,290, filed on Sep. 23, 2002, now Pat. No. 6,818,002, which is a continuation-in-part of application No. 09/867,307, filed on May 29, 2001, now Pat. No. 6,758,851, which is a continuation-in-part of application No. 09/654,934, filed on Sep. 1, 2000, now Pat. No. 6,482,215, which is a continuation-in-part of application No. 09/389,712, filed on Sep. 3, 1999, now Pat. No. 6,143,009, which is a continuation-in-part of application No. 09/241,802, filed on Feb. 2, 1999, now abandoned, application No. 10/423,677, which is a continuation-in-part of application No. 10/086,465, filed on Mar. 1, 2002, now Pat. No. 6,767,353.

(60) Provisional application No. 60/118,611, filed on Feb. 4, 1999.

(51) Int. Cl.
*A61B 17/22* (2006.01)
(52) U.S. Cl. ...................... 606/159; 606/167
(58) Field of Classification Search ............... 606/159, 606/180, 167–171; 15/104.095, 69, 71, 104.03, 15/104.05, 236.1, 88, 88.2, 104.09, 104.096; 600/564, 433–435; 604/22
See application file for complete search history.

(56) References Cited

U.S. PATENT DOCUMENTS

| | | | |
|---|---|---|---|
| 3,320,957 A | 5/1967 | Sokolik | |
| 3,614,953 A | 10/1971 | Moss | |
| 4,020,847 A * | 5/1977 | Clark, III | ................... 606/159 |
| 4,030,503 A | 6/1977 | Clark, III | |
| 4,228,802 A | 10/1980 | Trott | |
| 4,646,736 A | 3/1987 | Auth | |
| 4,679,557 A | 7/1987 | Opie et al. | |
| 4,772,258 A | 9/1988 | Marangoni | |
| 4,790,812 A | 12/1988 | Hawkins, Jr. et al. | |
| 4,857,046 A | 8/1989 | Stevens et al. | |
| 4,883,460 A | 11/1989 | Zanetti | |

(Continued)

*Primary Examiner*—Michael J. Hayes
*Assistant Examiner*—L. Bachman
(74) *Attorney, Agent, or Firm*—Samuel Shiber

(57) ABSTRACT

A vessel cleaning system for removing an obstruction from within a patient's vessel, the system comprising a housing, connected to a flexible-tube, a motor-driven flexible agitator-shaft rotatably disposed in the flexible-tube, and a flexible distal-agitator that is connected to the agitator-shaft and shaped so that it is asymmetrically offset to only one side of the longitudinal axis of the agitator-shaft. The agitator-shaft is extended from an open distal end of the flexible-tube to break the obstruction into pieces while rotating with an effective diameter that is larger than its cross-sectional diameter and the distal-agitator is made of a spiral wire, whereas the direction of its winding, relative to the direction of rotation, is such that the distal-agitator unscrews itself from tight engagements with its surroundings and automatically retracts into the flexible-tube.

3 Claims, 4 Drawing Sheets

U.S. PATENT DOCUMENTS

| | | |
|---|---|---|
| 4,923,462 A | 5/1990 | Stevens |
| 4,986,807 A | 1/1991 | Farr |
| 4,994,067 A | 2/1991 | Summers |
| 5,009,659 A | 4/1991 | Hamlin et al. |
| 5,078,722 A | 1/1992 | Stevens |
| 5,087,265 A | 2/1992 | Summers |
| 5,092,872 A | 3/1992 | Segalowitz |
| 5,100,426 A | 3/1992 | Nixon |
| 5,116,350 A | 5/1992 | Stevens |
| 5,135,531 A | 8/1992 | Shiber |
| 5,192,291 A | 3/1993 | Pannek |
| 5,217,474 A | 6/1993 | Zacca et al. |
| 5,242,460 A | 9/1993 | Klein et al. |
| 5,242,461 A | 9/1993 | Kortenbach et al. |
| 5,261,877 A | 11/1993 | Fine et al. |
| 5,269,751 A | 12/1993 | Kaliman et al. |
| 5,282,484 A | 2/1994 | Reger |
| 5,284,486 A | 2/1994 | Kotula et al. |
| 5,306,244 A | 4/1994 | Shiber |
| 5,312,425 A | 5/1994 | Evans et al. |
| 5,312,427 A | 5/1994 | Shturman |
| 5,314,407 A * | 5/1994 | Auth et al. .................. 604/22 |
| 5,314,438 A | 5/1994 | Shturman |
| 5,318,576 A | 6/1994 | Plassche, Jr. et al. |
| 5,334,211 A | 8/1994 | Shiber |
| 5,350,390 A | 9/1994 | Sher |
| 5,356,418 A * | 10/1994 | Shturman .................. 606/159 |
| 5,358,472 A | 10/1994 | Vance et al. |
| 5,358,485 A | 10/1994 | Vance et al. |
| 5,358,509 A | 10/1994 | Fine et al. |
| 5,366,464 A | 11/1994 | Belknap |
| 5,370,651 A | 12/1994 | Summers |
| 5,370,653 A | 12/1994 | Cragg |
| 5,376,100 A | 12/1994 | Lefebvre |
| 5,389,090 A | 2/1995 | Fischell |
| 5,395,311 A | 3/1995 | Andrews |
| 5,402,790 A | 4/1995 | Jang et al. |
| 5,403,334 A | 4/1995 | Evans et al. |
| 5,417,703 A | 5/1995 | Brown et al. |
| 5,423,799 A | 6/1995 | Shiu |
| 5,449,369 A | 9/1995 | Imran |
| 5,490,859 A | 2/1996 | Mische et al. |
| 5,501,694 A | 3/1996 | Resseman et al. |
| 5,507,292 A | 4/1996 | Jang et al. |
| 5,507,760 A | 4/1996 | Wynne et al. |
| 5,507,761 A | 4/1996 | Duer |
| 5,512,044 A | 4/1996 | Duer |
| 5,527,326 A | 6/1996 | Hermann et al. |
| 5,540,707 A | 7/1996 | Resseman et al. |
| 5,554,114 A | 9/1996 | Wallace et al. |
| 5,554,163 A | 9/1996 | Shturman |
| 5,556,405 A | 9/1996 | Lary |
| 5,556,408 A | 9/1996 | Farhat |
| 5,569,275 A | 10/1996 | Kotula et al. |
| 5,569,277 A | 10/1996 | Evans et al. |
| 5,571,130 A | 11/1996 | Simpson et al. |
| 5,584,843 A | 12/1996 | Wulfman et al. |
| 5,626,593 A | 5/1997 | Imran |
| 5,630,823 A | 5/1997 | Schmitz-Rode et al. |
| 5,632,755 A | 5/1997 | Nordgren et al. |
| 5,643,296 A | 7/1997 | Hundertmark et al. |
| 5,643,297 A | 7/1997 | Nordgren et al. |
| 5,643,298 A | 7/1997 | Nordgren et al. |
| 5,649,941 A | 7/1997 | Lary |
| 5,681,336 A | 10/1997 | Clement et al. |
| 5,688,234 A | 11/1997 | Frisbie |
| 5,695,506 A | 12/1997 | Pike et al. |
| 5,695,507 A | 12/1997 | Auth et al. |
| 5,695,508 A | 12/1997 | Chigogidze |
| 5,702,413 A | 12/1997 | Lafontaine |
| 5,785,675 A | 7/1998 | Drasler et al. |
| 5,843,103 A | 12/1998 | Wulfman |
| 5,873,882 A | 2/1999 | Straub et al. |
| 5,876,414 A | 3/1999 | Straub |
| 5,897,534 A | 4/1999 | Heim et al. |
| 5,954,737 A | 9/1999 | Lee |
| 6,090,118 A * | 7/2000 | McGuckin, Jr. ............ 606/159 |
| 6,143,009 A | 11/2000 | Shiber |
| 6,312,438 B1 | 11/2001 | Adams |
| 6,322,572 B1 | 11/2001 | Lee |
| 6,494,890 B1 * | 12/2002 | Shturman et al. ........... 606/159 |
| 6,602,264 B1 | 8/2003 | McGuckin |
| 6,824,550 B1 * | 11/2004 | Noriega et al. ............. 606/159 |

* cited by examiner

VESSEL CLEANING SYSTEM WITH ASYMMETRICAL AUTO RETRACTING AGITATOR

CROSS REFERENCE TO OTHER APPLICATIONS

This application is a continuation-in-part (CIP) of my application Ser. No. 10/252,290 filed on Sep. 23, 2002, now U.S. Pat. No. 6,818,002 that is a CIP of my earlier application Ser. No. 09/867,307 filed on May 29, 2001, now U.S. Pat. No. 6,758,851 that is a CIP of my earlier application Ser. No. 09/654,934 filed on Sep. 1, 2000; now U.S. Pat. No. 6,482,215 that is a CIP of my earlier application Ser. No. 09/389,712 filed on Sep. 3, 1999, now U.S. Pat. No. 6,143,009 that is a CIP of Ser. No. 09/241,802 filed on Feb. 2, 1999; now abandoned. This application also relies for priority on my international patent application No. PCT/US00/01797 filed on Jan. 25, 2000 that relies for priority on the above mentioned patent application Ser. No. 09/389,712 and Ser. No. 09/241,802, and on a provisional application Ser. No. 60/118,611 filed on Feb. 4, 1999, and on my international patent application No. PCT/US03/05717, filed on 25 Feb., 2003. Additionally, this application is a CIP of my earlier application Ser. No. 10/086,465 filed on Mar. 1, 2002, now U.S. Pat. No. 6,767,353.

All the above prior applications are herein incorporated by reference.

BACKGROUND AND SUMMARY OF THE INVENTION

The vessel cleaning system is designed for removing an obstruction from within a patient's vessel through a tube of small diameter and particularly for opening vessels, such as blood vessels, that tend to become obstructed by a thrombus.

Current treatments such as pharmacological, surgical or trans-catheter procedures can be time-consuming, traumatic and expensive. Thus, objects of the present invention are to simplify, improve and shorten the procedure by enabling the physician to navigate and advance the system through obstructions, curved vessels and bifurcations and then break the obstruction into small pieces that can be removed through a tube by suction and by mechanical means. To further reduce the likelihood that the pieces of the obstruction are carried downstream into the vasculature, the system can be delivered and guided through a catheter with an inflatable distal barrier so that the flow through the vessel can be temporarily occluded during the procedure.

The system comprises a housing that is connected to a flexible-tube, a motor-driven flexible agitator-shaft that is rotatably disposed in the flexible-tube, and an offset distal-agitator connected to the agitator-shaft. The distal-agitator extends out of the open distal end of the flexible-tube to break the obstruction into pieces while rotating with an effective diameter that is larger than its cross-sectional diameter.

The distal-agitator is preferably made of a flattened wire wound on its flat side to form a spiral. A distal-tip of the distal-agitator is rounded to minimize trauma to the vessel's wall. The distal-tip is preferably formed by melting the spiral wire and allowing it to re-solidify.

The direction of the winding relative to the direction of rotation of the distal-agitator is chosen so that it automatically unscrews from tight engagements with its surroundings similarly to a corkscrew releasing itself from engagement with a cork.

The agitator-shaft can be made, at least partially, of a spiral wire that is preferably a continuation of the wire from which the distal-agitator is made of. A spacing between coils of the spiral wire make the agitator-shaft longitudinally compressible so that the distal-agitator can retract into the flexible-tube when it unscrews itself from a tight engagement with its surroundings. Further, in response to an elevated torque that the agitator-shaft transmits, to unscrew the distal-agitator from the tight engagement, the agitator-shaft tends to contract both diametrically and longitudinally, thereby pulling the distal-agitator into the flexible-tube.

While the agitator-shaft is preferably made to be able to contract longitudinally, the extent it can expand longitudinally can be limited by adding a central tension member that is connected to the proximal and distal ends of the agitator-shaft.

The distal-agitator is a short flexible curved section that extends out the flexible tube and is asymmetrically offset to only one side of the longitudinal axis of the agitator-shaft. Upon encountering a hard or tight spot in the obstructed vessel such asymmetrical construction is able to rotate around a shifted axis with a decreased effective diameter so that it can be rotated with less torque as compared with a symmetrical distal agitator (it can be appreciated that if the offset was symmetrical, the shifting of the axis would not decrease the effective diameter).

It also can be appreciated that since the distal-agitator is flexible, the offset can decrease due to a reaction force applied to it by the vessel's wall or, it can dynamically increase due to centrifugal force acting on its asymmetrical structure.

The agitator-shaft radially supports the flexible-tube in which it rotates while the system is operated in curved vessels.

The system is inserted into the vessel directly (e.g., when access to the vessel is gained surgically) or through an introducer. The introducer comprises a first side port that can be utilized to either inject or aspirate fluids and particles into or from the vessel.

Optionally, a catheter can be used to guide the system into the vessel. Such catheter can comprise a toroidal barrier at its distal end section for temporarily blocking flow between the catheter and the vessel. This allows the system to macerate and remove the obstructing material while avoiding release of obstruction particles downstream.

A passageway, defined through the system's housing, connects the flexible-tube with an external port so that the port can be utilized to inject or aspirate fluids and particles into or from the vessel, respectively.

The agitator-shaft is mechanically connected to an output shaft of the motor by a coupling. The coupling is made of an insolating material that minimizes electrical and electromagnetic energy transfer from the motor output shaft through the agitator-shaft to the patient and the surroundings.

The motor has a casing, at least a portion of which is made of conductive material, e.g., of metal. The motor is connected to a first wire and a second wire that supply electrical power to cause the motor's output shaft to rotate. To minimize the generation and emission of electromagnetic energy, a first capacitance is interposed between the portion of the motor's casing that is made of conductive material and the first wire, a second capacitance is interposed between the portion of the casing that is made of conductive material and the second wire, and a third capacitance is interposed between the first and the second wires.

To prevent the flexible-tube from kinking (i.e., diametrically collapsing) and to prevent the agitator-shaft from being sharply bent at the point in which they are connected to the housing, their radius of bending is limited to a radius of curvature of a wall of a depression defined by the housing that surrounds the tubes. Optionally, the depression can be formed in a separate block that is pressed into the housing, after the outer tube has been bonded to the housing, to reduce the likelihood of any residue of the bonding process deforming the curvature defined by the radius of the wall.

The system can be manufactured in varying lengths and diameters to reach and treat different locations in the human anatomy and different conditions of occlusive diseases, as well as to suit variations in the methods of use and physicians' preferences of operating the device.

To remove an obstruction from within a patient's vessel, a system, according to the present invention, is advanced into the vessel and the motor is activated to rotate the agitator-shaft, which in turn rotates the distal-agitator, breaking the obstruction to pieces. As the distal-agitator is rotated at the speed that is sufficient to break the obstruction to pieces, the centrifugal force acting on the asymmetrical distal-agitator tends to increase its effective diameter by elastically deforming it.

The system can be inserted into the vessel directly (e.g., when used intraoperatively where direct access to the vessel is gained surgically), or percutaneously through an introducer or through a catheter especially when using a long system, e.g., a system that is introduced through the skin at the groin area and is guided from the groin area with a catheter to vessels serving the heart or brain.

DETAILED DESCRIPTION OF THE DRAWINGS

FIGS. 1 to 6 show a vessel cleaning system 10, embodying the present invention, for removing an obstruction 11 from a patient's vessel 12 through a small diameter flexible-tube 13, and particularly, for opening vessels, such as blood vessels and grafts, that tend to become obstructed by a thrombus.

Figure 2:
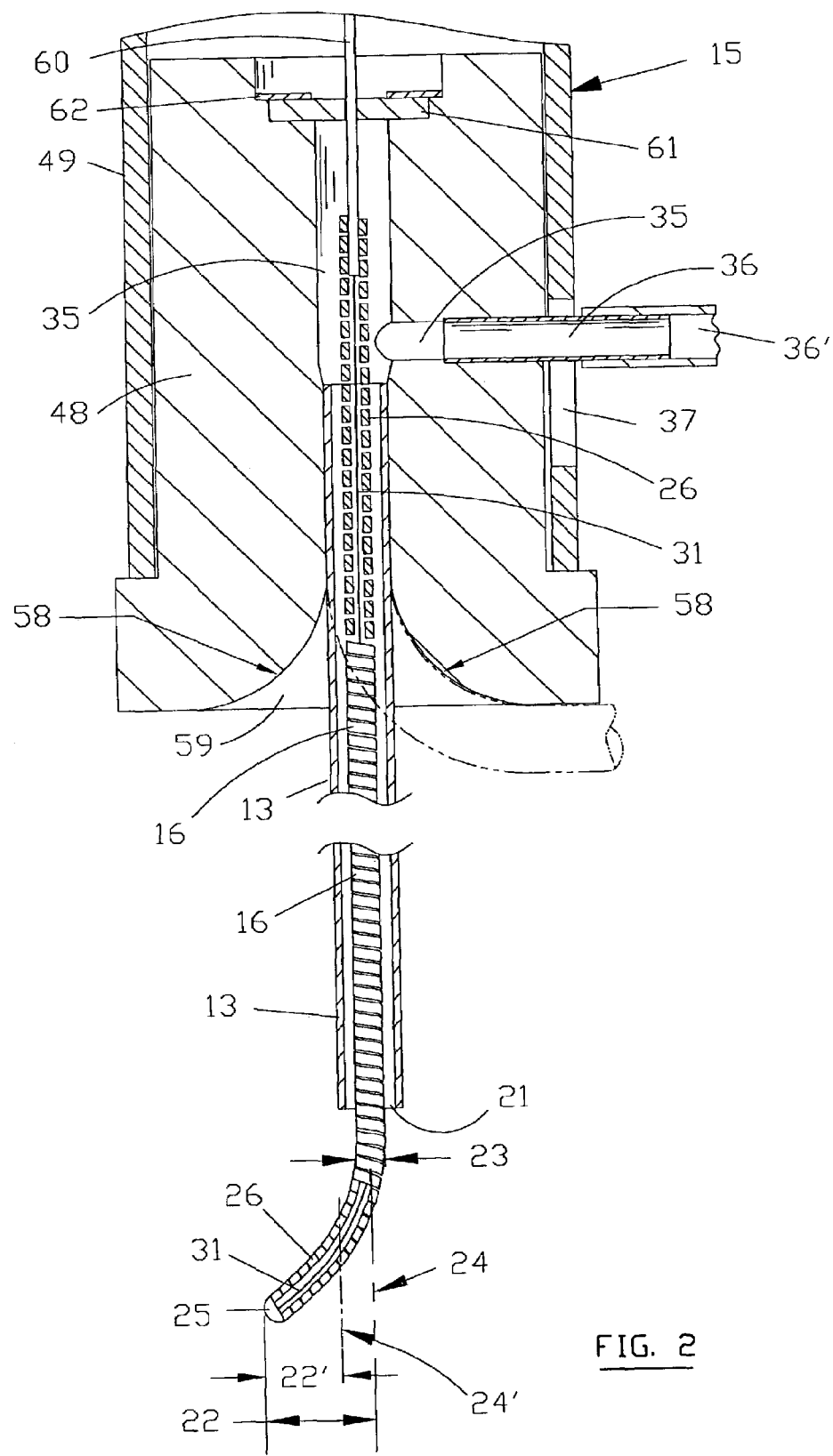
FIG. 2 is a partially sectioned schematic side view of distal and proximal sections of the flexible agitator-shaft and adjacent portions of the system
Figure 2A:
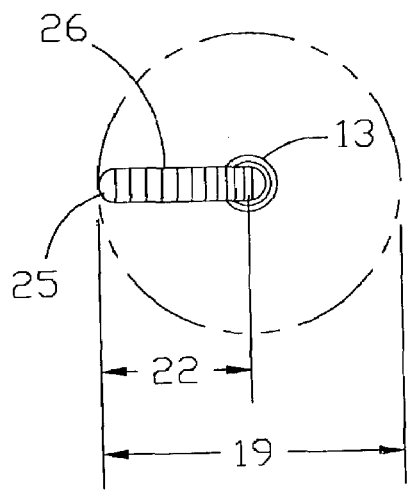
FIGS. 2a and 2c show the same system as in FIG. 2 viewed from a point distal to the system.
Figure 2B:
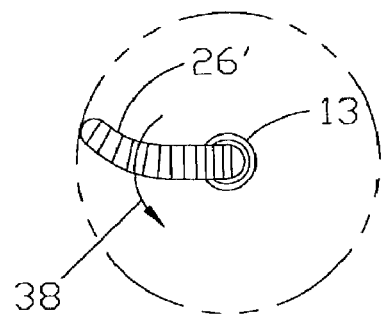
FIG. 2b show a slightly modified system as in FIG. 2 with the distal tip having a three dimensional curve viewed from a point distal to the system.
Figure 2C:
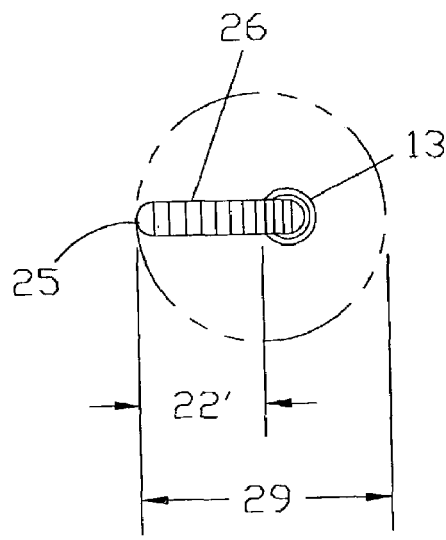
Figure 4:
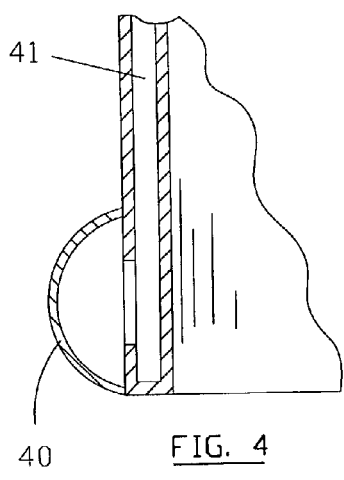
FIG. 4 is an enlarged sectioned schematic side view of the distal section of the catheter that is encircled by a phantom line in FIG. 1 with the barrier being inflated.
Figure 5:
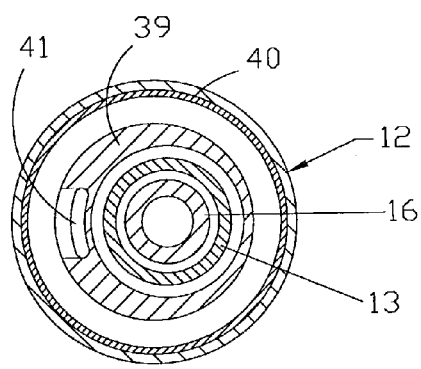
FIG. 5 is a sectioned schematic view of the catheter along line 5-5 marked in FIG. 1 with the barrier being deflated.
Figure 6:
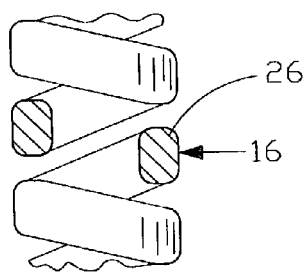
FIG. 6 is a sectioned schematic view of a portion of the agitator-shaft illustrating the cross-section of the flat wire from which the spiral is preferably wound.

A motor 14 is located in a housing 15 that is connected to the proximal end of the flexible-tube ("proximal" indicates a part of the system that is closer to the physician whereas "distal" indicates that it is further into the vessel). The flexible-tube has an open distal end 21. A motor-driven flexible agitator-shaft 16 is rotatably disposed in the flexible-tube and is connected to an offset distal-agitator 20. The distal-agitator is a short flexible section that extends from the open distal end to one side of the longitudinal axis of the agitator-shaft 24 (note FIG. 2) to form an asymmetrical offset 22. As the distal-agitator rotates, it breaks the obstruction, that is within its effective diameter, to pieces. The effective diameter of the distal-agitator is larger than a cross-sectional diameter 23 of the distal-agitator (note FIG. 2). For example, when the distal agitator rotates around an axis 24, the effective diameter 19 is about twice the offset 22 (note FIG. 2a). Due to the asymmetrical shape of the distal-agitator it extends from the open distal end to one side of the longitudinal axis of the agitator-shaft. It should be understood that as the distal-agitator rotates, the imaginary plane on which it is depicted in FIG. 2, rotates with it so that at any given time the distal-agitator extends only to one side of the longitudinal axis of the agitator-shaft. However, the curvature of the distal-agitator is not limited to this imaginary plane, for example, it can be curved so that its tip slightly drags behind this plane as it rotates in direction 38 to soften its contact with the surrounding vessel (note 26' in FIG. 2b). Due to dynamic considerations or when operating in a tight region of the obstructed vessel, the asymmetrical shape, together with the flexibility of the agitator-shaft 16 and of the tube 13, allows the distal-agitator to rotate around an axis 24' with a reduced offset 22' and reduced effective diameter 29 (note FIG. 2c) so it can be rotated with less torque as compared with torque that would have been required to rotate a symmetrical distal-agitator with same offset (because, as would be appreciated by one skilled in the art, with a symmetrical offset the shifting of the axis of rotation from 24 to 24' would not reduce the effective diameter).

It also can be appreciated that since the distal-agitator is flexible, the offset can decrease due to a reaction force applied to it by obstruction or the vessel's wall or, it can increase due to centrifugal force acting on its asymmetrical structure, thereby dynamically increasing the effective diameter.

The distal-agitator is preferably made of a flattened spiral wire 26 that is wound on its flat side into a spiral. Flat wire commonly has a pair of opposing flat sides and a pair of rounded sides since it is commonly produced by pulling a round wire through a pair of adjacent rollers. However, a flat wire can also have a more rectangular cross section, in which case the wire is preferably wound on its longer flat side (note FIG. 6).

The direction of the winding relative to the direction in which the spiral is rotated by the motor is such that the distal-agitator automatically unscrews itself from tight engagements with its surroundings similarly to a corkscrew releasing itself from engagement with a cork while it is being rotated by the motor.

The agitator-shaft is also preferably made of a spiral wire that is preferably a continuation of the spiral wire from which the distal-agitator is made. Such one-piece construction does not have a joint that may be prone to failure. The agitator-shaft is longitudinally compressible so that the distal-agitator can retract into the flexible-tube when it unscrews itself from tight engagements with its surroundings. Further, in response to the distal-agitator becoming tightly engaged with its surroundings, an elevated torque level appears in the agitator-shaft, causing it to longitudinally contract and pull the distal-agitator into the flexible-tube.

While the agitator-shaft can contract longitudinally, the extent it expands longitudinally can be optionally limited by a tension member in the form of a stainless steel wire or a multi-strand cable 31 that is disposed in the agitator-shaft. A proximal end of the tension member is connected to a distal end of a small diameter hollow shaft 60 that fits inside and is connected to the proximal end of the agitator-shaft. The distal end of the tension member is connected to the distal end of the agitator-shaft or to a distal tip 25 of the distal-agitator (note FIG. 2).

A seal 61 that is backed and secured in place by a washer 62 allows the shaft 60 to rotate and slide while containing negative or positive pressure that prevails in the passageway 35 from reaching the housing containing the motor.

The distal-tip 25 of the distal-agitator is rounded to minimize trauma to the vessel in which it operates in. The rounded tip is preferably formed by melting the distal-tip of the spiral wire and allowing it to re-solidify to a rounded shape. Optionally, the distal end of the cable 31 can be anchored to the distal-tip during the same process (note FIG. 2).

Figure 1:
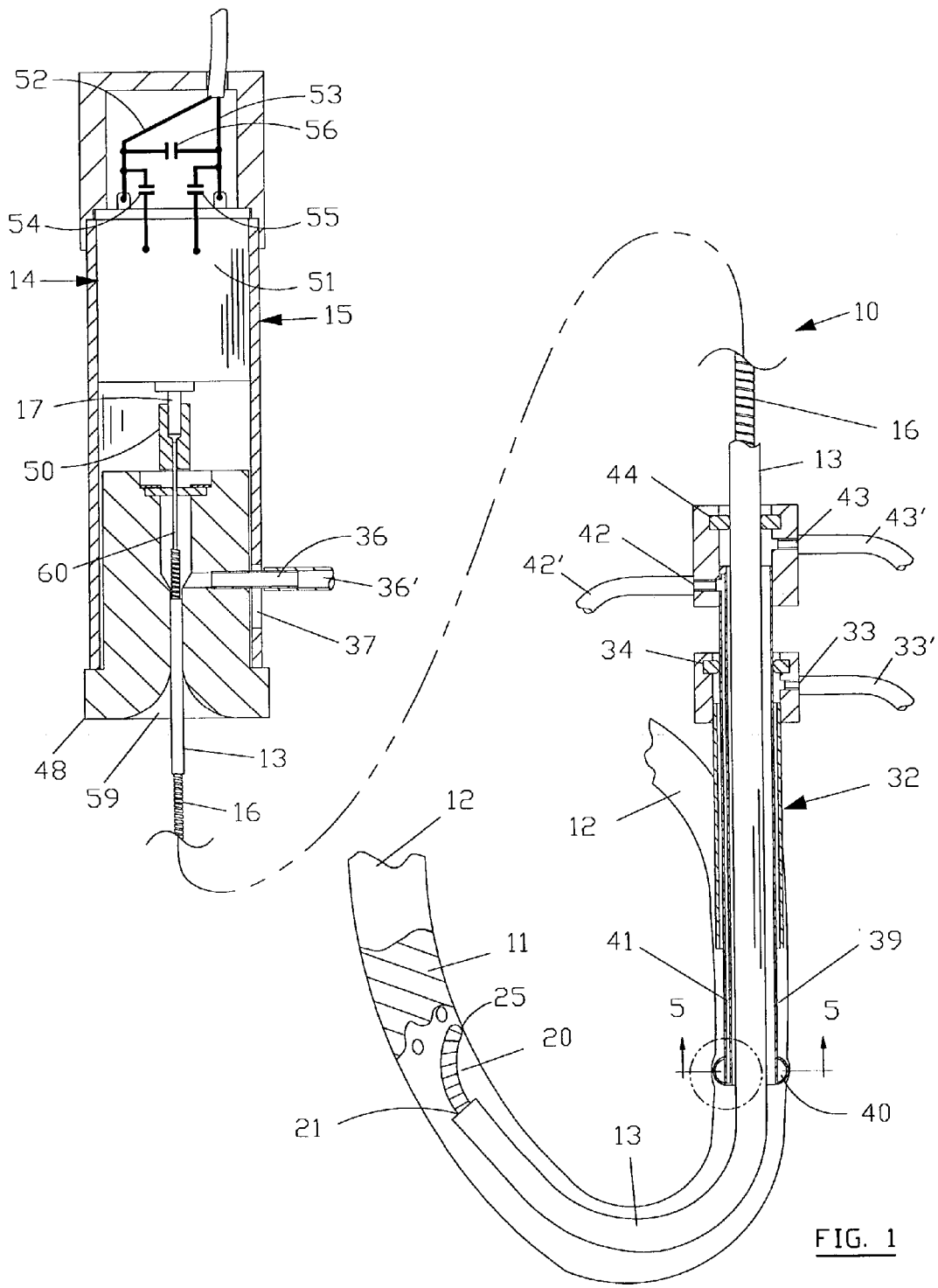
FIG. 1 is a partially sectioned schematic side view of the system, embodying the present invention, inserted into an obstructed vessel through a catheter with an inflated distal barrier and through an introducer; the offset distal-agitator is shown in an extended position. The distal section of the system is shown in an enlarged scale (compared with the proximal section). The mid-section is represented by a phantom line.
Figure 3:
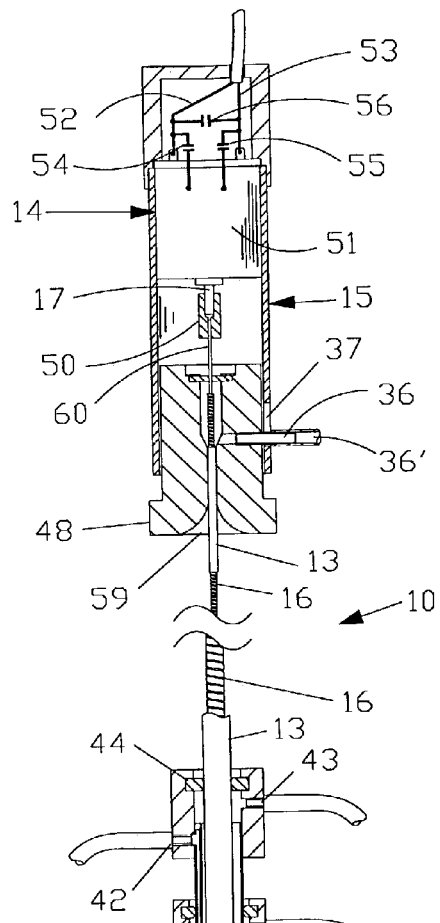
FIG. 3 shows the same system as in FIG. 1 with the barrier deflated and the distal-agitator retracted.
Figure 3:
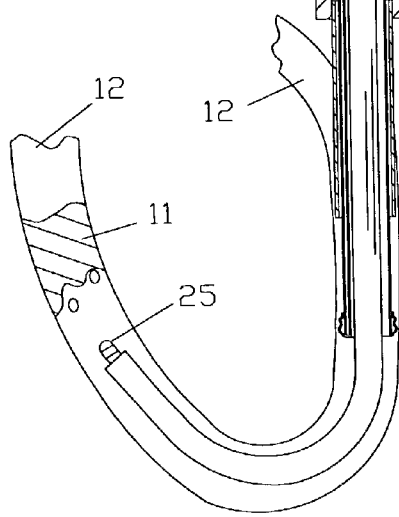

The passageway 35 that is defined through the housing, connects an external port, containing a stainless steel tube section 36, to the flexible-tube 36' so that fluids or particles can be injected into or aspirated from the vessel. The tube section 36 and a slot 37 permit the distal part 48 of the housing and the mid section 49 of the housing to move relative to each other in order to extend or retract the distal-agitator as shown in FIGS. 1 and 3, respectively.

The system can be inserted into the vessel directly (e.g., when access to the vessel is gained surgically), or through a standard introducer 32. The introducer has a first side port 33, connected to a tube 33', that can be utilized to inject fluid and particles into, or to aspirate them from the vessel. A seal 34 prevents fluid leakage through the proximal end of the introducer.

Optionally, the system can be inserted into the vessel through a catheter 39 that can be used to guide the system to the vessel through the patient's vasculature. Such a catheter can be equipped with a toroidal barrier 40 at its distal end section that temporarily blocks flow in the vessel when the barrier is inflated through an inflation lumen 41 that connects the barrier 40 to an inflation port 42 and a tube 42' (note FIGS. 1, 4 and 5). This allows the system to macerate and remove the obstructing material while the vessel is blocked, avoiding release of obstruction particles downstream.

The catheter also comprises a second side port 43 connected to a tube 43' that can be used to inject fluid and particles into, or to aspirate them from the vessel. A seal 44 prevents fluid leakage around the proximal end of the catheter.

A proximal end of the agitator-shaft is connected to a small diameter shaft 60 that is connected by a coupling 50 to the output shaft 17 of the motor. The coupling 50 is made of insolating material to minimize transmission of electrical and electromagnetic energy from the motor output shaft to the agitator-shaft. It is appreciated that because of its elongated design, the agitator-shaft tends to act as an antenna for such electromagnetic energy unless properly isolated from the motor.

The motor is connected to a source of electric energy through a pair of wires 52 and 53. At least a portion of the motor's casing 51 is made of conductive material. To reduce emission of electromagnetic energy, a first capacitance 54 is interposed between the portion of the casing that is made of conductive material and the first wire, a second capacitance 55 is interposed between the portion of the casing that is made of conductive material and the second wire, and a third capacitance 56 is interposed between the wires 52 and 53.

The agitator-shaft radially supports the flexible-tube in which it rotates, preventing it from kinking (i.e., diametrically collapsing) particularly while the system is used in a curved vessel. To further prevent the flexible-tube from kinking and to prevent the agitator-shaft from being sharply bent at the point in which they are connected to the distal part of the housing 48, their radius of bending is limited by a radius of curvature 58 of a wall of a depression 59 defined in the proximal part of the housing that surrounds the tube 13 and acts as a passive strain limiter.

The system can be manufactured in varying diameters and length to reach and treat vessels of different diameter in different locations of the human anatomy, as well as to suit variations in the use and preferences of physicians' mode of operation of the device.

One method of using the system entails advancing it into the vessel and activating the motor to rotate the flexible agitator-shaft which in turn rotates the distal-agitator thereby breaking the obstruction into pieces. As the distal-agitator is rotated at the speed that is sufficient to break the obstruction into pieces, the centrifugal force acting on the asymmetrical distal-agitator tends to enhance its effective diameter by elastically deforming it. Fluids, such as saline solution mixed with radio-opaque contrast media and heparin, can be injected into the vessel through first or second ports 33 or 43, or through the tube section 36, passageway 35, and the flexible-tube 13. Alternatively, the above ports and the tube section can be used to aspirate fluids and obstruction particles from the vessel. If the particles are aspirated through the flexible-tube 13, the relative motion between the rotating agitator-shaft and the flexible-tube reduces friction that may resist the movement of the pieces through the flexible-tube.

The system can be inserted into the vessel directly (e.g., when used intraoperatively where direct access to the vessel is gained surgically), or percutaneously through an introducer or through a catheter, especially when using a long system (e.g., a system that is introduced through the skin at the groin area and is guided from the groin area to vessels serving the heart or the brain).

The direction of the winding of the distal-agitator relative to the direction of rotation is such that it automatically unscrews itself from tight engagements with its surroundings and automatically retracts as it rotates. In addition, the torque carried through the distal-agitator and the agitator-shaft slightly decreases their diameters, making it less likely that the shaft would bind with the flexible-tube or that the distal-agitator would bind with its surroundings.

I claim:

1. A method for removing an obstruction from within a patient's vessel comprising:
    inserting into the vessel a vessel cleaning system having a housing connected to a flexible-tube with an open distal end, a motor-driven flexible agitator-shaft rotatably disposed in the flexible-tube, and an offset distal-agitator connected to the agitator-shaft extending from the open distal end, whereas the distal-agitator is at least partially made of a spiral wire winding; and rotating the distal-agitator with an effective diameter that is larger than its cross-sectional diameter at a speed sufficient to break the obstruction into pieces and in a direction, relative to the direction of the winding of the distal-agitator, such that the distal-agitator unscrews itself from tight engagements with its surroundings and automatically retracts in a proximal direction into the flexible tube.

2. As in claim 1 wherein the vessel cleaning system is advanced into the vessel through an introducer or a catheter.

3. As in claim 1 wherein the distal-agitator is rotated at such speed that a centrifugal force elastically deforms it and increases the effective diameter.

* * * * *